US008753325B2

(12) United States Patent
Lev et al.

(10) Patent No.: US 8,753,325 B2
(45) Date of Patent: Jun. 17, 2014

(54) LIQUID DRUG TRANSFER DEVICE WITH VENTED VIAL ADAPTER

(75) Inventors: Nimrod Lev, Savion (IL); Amir Lev, Kfar Saba (IL); Niv Ben Shalom, Netanya (IL)

(73) Assignee: MEDIMOP Medical Projects, Ltd., Ra'anana (IL)

( * ) Notice: Subject to any disclaimer, the term of this patent is extended or adjusted under 35 U.S.C. 154(b) by 0 days.

(21) Appl. No.: 13/576,461

(22) PCT Filed: Feb. 23, 2011

(86) PCT No.: PCT/IL2011/000187
§ 371 (c)(1),
(2), (4) Date: Aug. 1, 2012

(87) PCT Pub. No.: WO2011/104712
PCT Pub. Date: Sep. 1, 2011

(65) Prior Publication Data
US 2013/0046269 A1 Feb. 21, 2013

(30) Foreign Application Priority Data
Feb. 24, 2010 (IL) ........................................ 204141
Nov. 4, 2010 (IL) ........................................ 209101

(51) Int. Cl.
*A61B 19/00* (2006.01)

(52) U.S. Cl.
USPC ........... 604/405; 604/403; 604/406; 604/411; 604/412; 604/414

(58) Field of Classification Search
CPC . A61J 1/2096; A61J 1/2089; A61J 2001/201; A61J 2001/2055; A61J 2001/2075; A61J 2001/2082; A61J 2001/2013; A61J 2001/2065; A61J 2001/2068; A61J 2001/2079; A61B 19/00
USPC ................................................. 604/403–416
See application file for complete search history.

(56) References Cited

U.S. PATENT DOCUMENTS

| | | | |
|---|---|---|---|
| 62,333 | A | 2/1867 | Holl |
| 1,021,681 | A | 3/1912 | Jennings |
| 1,704,817 | A | 3/1929 | Ayers |

(Continued)

FOREIGN PATENT DOCUMENTS

| | | | |
|---|---|---|---|
| DE | 1913926 | A1 | 9/1970 |
| DE | 4122476 | A1 | 1/1993 |

(Continued)

OTHER PUBLICATIONS

Int'l Search Report issued Jan. 22, 2013 in Int'l Application No. PCT/IL2012/000354.

(Continued)

*Primary Examiner* — Philip R Wiest
*Assistant Examiner* — Ariana Zimbouski
(74) *Attorney, Agent, or Firm* — Panitch Schwarze Belisario & Nadel LLP

(57) ABSTRACT

Liquid drug transfer devices including a vented vial adapter having a top wall, a downward depending skirt, and a dual lumen puncturing spike. The top wall includes vent apertures in flow communication with an underlying air filter and protective hoods for covering the vent apertures from splashes. The hood-like hoods are preferably quarter sphere shaped with hood apertures facing radial outwards.

5 Claims, 3 Drawing Sheets

(56) References Cited

U.S. PATENT DOCUMENTS

| | | | | |
|---|---|---|---|---|
| 1,930,944 | A | 10/1933 | Schmitz, Jr. | |
| 2,326,490 | A | 8/1943 | Perelson | |
| 2,931,668 | A | 4/1960 | Baley | |
| 2,968,497 | A | 1/1961 | Treleman | |
| 3,059,643 | A | 10/1962 | Barton | |
| D198,499 | S | 6/1964 | Harautuneian | |
| 3,484,849 | A | 12/1969 | Huebner et al. | |
| 3,618,637 | A | 11/1971 | Santomieri | |
| 3,757,981 | A | 9/1973 | Harris, Sr. et al. | |
| 3,788,524 | A | 1/1974 | Davis et al. | |
| 3,822,700 | A | 7/1974 | Pennington | |
| 3,826,261 | A | 7/1974 | Killinger | |
| 3,885,607 | A | 5/1975 | Peltier | |
| 3,938,520 | A | 2/1976 | Scislowicz et al. | |
| 3,957,052 | A | 5/1976 | Topham | |
| 3,977,555 | A | 8/1976 | Larson | |
| 3,993,063 | A | 11/1976 | Larrabee | |
| 4,020,839 | A | 5/1977 | Klapp | |
| 4,051,852 | A | 10/1977 | Villari | |
| 4,109,670 | A | 8/1978 | Slagel | |
| 4,121,585 | A | 10/1978 | Becker, Jr. | |
| 4,161,178 | A | 7/1979 | Genese | |
| 4,187,848 | A | 2/1980 | Taylor | |
| 4,203,067 | A | 5/1980 | Fitzky et al. | |
| 4,203,443 | A | 5/1980 | Genese | |
| 4,210,173 | A | 7/1980 | Choksi et al. | |
| D257,286 | S | 10/1980 | Folkman | |
| 4,253,501 | A | 3/1981 | Ogle | |
| 4,296,786 | A | 10/1981 | Brignola | |
| 4,303,067 | A | 12/1981 | Connolly et al. | |
| 4,312,349 | A | 1/1982 | Cohen | |
| 4,314,586 | A | 2/1982 | Folkman | |
| 4,328,802 | A | 5/1982 | Curley et al. | |
| 4,335,717 | A | 6/1982 | Bujan et al. | |
| D267,199 | S | 12/1982 | Koenig | |
| 4,376,634 | A | 3/1983 | Prior et al. | |
| D268,871 | S | 5/1983 | Benham et al. | |
| 4,392,850 | A | 7/1983 | Elias et al. | |
| 4,410,321 | A | 10/1983 | Pearson et al. | |
| 4,411,662 | A | 10/1983 | Pearson | |
| D271,421 | S | 11/1983 | Fetterman | |
| 4,434,823 | A | 3/1984 | Hudspith | |
| 4,465,471 | A | 8/1984 | Harris et al. | |
| 4,475,915 | A | 10/1984 | Sloane | |
| 4,493,348 | A | 1/1985 | Lemmons | |
| 4,505,709 | A | 3/1985 | Froning et al. | |
| 4,507,113 | A | 3/1985 | Dunlap | |
| D280,018 | S | 8/1985 | Scott | |
| 4,532,969 | A | 8/1985 | Kwaan | |
| 4,564,054 | A | 1/1986 | Gustavsson | |
| 4,573,993 | A | 3/1986 | Hoag et al. | |
| 4,576,211 | A | 3/1986 | Valentini et al. | |
| 4,581,014 | A | 4/1986 | Millerd et al. | |
| 4,588,396 | A | 5/1986 | Stroebel et al. | |
| 4,588,403 | A | 5/1986 | Weiss et al. | |
| D284,603 | S | 7/1986 | Loignon | |
| 4,604,093 | A | 8/1986 | Brown et al. | |
| 4,607,671 | A | 8/1986 | Aalto et al. | |
| 4,614,437 | A | 9/1986 | Buehler | |
| 4,638,975 | A | 1/1987 | Iuchi et al. | |
| 4,639,019 | A | 1/1987 | Mittleman | |
| 4,667,927 | A | 5/1987 | Oscarsson | |
| 4,676,530 | A | 6/1987 | Nordgren et al. | |
| 4,683,975 | A | 8/1987 | Booth et al. | |
| 4,697,622 | A | 10/1987 | Swift et al. | |
| 4,721,133 | A | 1/1988 | Sundblom | |
| 4,729,401 | A | 3/1988 | Raines | |
| 4,735,608 | A | 4/1988 | Sardam | |
| 4,743,229 | A | 5/1988 | Chu | |
| 4,743,243 | A | 5/1988 | Vaillancourt | |
| 4,752,292 | A | 6/1988 | Lopez et al. | |
| 4,758,235 | A | 7/1988 | Tu | |
| 4,759,756 | A | 7/1988 | Forman et al. | |
| 4,778,447 | A | 10/1988 | Velde et al. | |
| 4,787,898 | A | 11/1988 | Raines | |
| 4,797,898 | A | 1/1989 | Martinez | |
| 4,804,366 | A | 2/1989 | Zdeb et al. | |
| 4,832,690 | A | 5/1989 | Kuu | |
| 4,834,152 | A * | 5/1989 | Howson et al. | 141/286 |
| 4,857,062 | A | 8/1989 | Russell | |
| 4,865,592 | A | 9/1989 | Rycroft | |
| 4,909,290 | A | 3/1990 | Coccia | |
| 4,931,040 | A | 6/1990 | Haber et al. | |
| 4,932,944 | A | 6/1990 | Jagger et al. | |
| 4,967,797 | A | 11/1990 | Manska | |
| D314,050 | S | 1/1991 | Sone | |
| D314,622 | S | 2/1991 | Andersson et al. | |
| 4,997,430 | A | 3/1991 | Van der Heiden et al. | |
| 5,006,114 | A | 4/1991 | Rogers et al. | |
| 5,035,686 | A | 7/1991 | Crittenden et al. | |
| 5,041,105 | A | 8/1991 | D'Alo et al. | |
| 5,045,066 | A | 9/1991 | Scheuble et al. | |
| 5,049,129 | A | 9/1991 | Zdeb et al. | |
| 5,053,015 | A | 10/1991 | Gross | |
| 5,061,248 | A | 10/1991 | Sacco | |
| 5,088,996 | A | 2/1992 | Kopfer et al. | |
| 5,096,575 | A | 3/1992 | Cosack | |
| 5,104,387 | A | 4/1992 | Pokorney et al. | |
| 5,113,904 | A | 5/1992 | Aslanian | |
| 5,122,124 | A | 6/1992 | Novacek et al. | |
| 5,125,908 | A | 6/1992 | Cohen | |
| 5,125,915 | A | 6/1992 | Berry et al. | |
| D328,788 | S | 8/1992 | Sagae et al. | |
| 5,171,230 | A | 12/1992 | Eland et al. | |
| 5,201,705 | A | 4/1993 | Berglund et al. | |
| 5,201,717 | A | 4/1993 | Wyatt et al. | |
| 5,203,771 | A | 4/1993 | Melker et al. | |
| 5,203,775 | A | 4/1993 | Frank et al. | |
| 5,211,638 | A | 5/1993 | Dudar et al. | |
| 5,232,029 | A | 8/1993 | Knox et al. | |
| 5,232,109 | A | 8/1993 | Tirrell et al. | |
| 5,242,432 | A | 9/1993 | DeFrank | |
| 5,247,972 | A | 9/1993 | Tetreault | |
| D341,420 | S | 11/1993 | Conn | |
| 5,269,768 | A | 12/1993 | Cheung | |
| 5,270,219 | A | 12/1993 | DeCastro et al. | |
| 5,279,576 | A | 1/1994 | Loo et al. | |
| 5,288,290 | A | 2/1994 | Brody | |
| 5,300,034 | A | 4/1994 | Behnke et al. | |
| 5,304,163 | A | 4/1994 | Bonnici et al. | |
| 5,308,483 | A | 5/1994 | Sklar et al. | |
| 5,312,377 | A | 5/1994 | Dalton | |
| 5,328,474 | A | 7/1994 | Raines | |
| D349,648 | S | 8/1994 | Tirrell et al. | |
| 5,334,163 | A | 8/1994 | Sinnett | |
| 5,334,179 | A | 8/1994 | Poli et al. | |
| 5,342,346 | A | 8/1994 | Honda et al. | |
| 5,344,417 | A | 9/1994 | Wadsworth, Jr. | |
| 5,350,372 | A | 9/1994 | Ikeda et al. | |
| 5,364,386 | A | 11/1994 | Fukuoka et al. | |
| 5,364,387 | A | 11/1994 | Sweeney | |
| 5,374,264 | A | 12/1994 | Wadsworth, Jr. | |
| 5,385,547 | A | 1/1995 | Wong et al. | |
| 5,397,303 | A | 3/1995 | Sancoff et al. | |
| 5,429,614 | A | 7/1995 | Fowles et al. | |
| 5,433,330 | A | 7/1995 | Yatsko et al. | |
| 5,445,630 | A | 8/1995 | Richmond | |
| 5,445,631 | A | 8/1995 | Uchida | |
| 5,451,374 | A | 9/1995 | Molina | |
| 5,454,805 | A | 10/1995 | Brony | |
| 5,464,111 | A | 11/1995 | Vacek et al. | |
| 5,464,123 | A | 11/1995 | Scarrow | |
| 5,466,219 | A | 11/1995 | Lynn et al. | |
| 5,466,220 | A | 11/1995 | Brenneman | |
| 5,470,327 | A | 11/1995 | Helgren et al. | |
| 5,478,337 | A | 12/1995 | Okamoto et al. | |
| 5,492,147 | A | 2/1996 | Challender et al. | |
| D369,406 | S | 4/1996 | Niedospial et al. | |
| 5,505,714 | A | 4/1996 | Dassa et al. | |
| 5,509,433 | A | 4/1996 | Paradis | |
| 5,520,659 | A | 5/1996 | Hedges | |
| 5,526,853 | A | 6/1996 | McPhee et al. | |
| 5,527,306 | A | 6/1996 | Haining | |
| 5,531,695 | A | 7/1996 | Swisher | |

(56) References Cited

U.S. PATENT DOCUMENTS

| | | | |
|---|---|---|---|
| 5,547,471 | A | 8/1996 | Thompson et al. |
| 5,549,577 | A | 8/1996 | Siegel et al. |
| 5,554,128 | A | 9/1996 | Hedges |
| 5,566,729 | A | 10/1996 | Grabenkort et al. |
| 5,569,191 | A | 10/1996 | Meyer |
| 5,573,281 | A | 11/1996 | Keller |
| 5,578,015 | A | 11/1996 | Robb |
| 5,583,052 | A | 12/1996 | Portnoff et al. |
| 5,584,819 | A | 12/1996 | Kopfer |
| 5,591,143 | A | 1/1997 | Trombley, III et al. |
| 5,603,706 | A | 2/1997 | Wyatt et al. |
| 5,607,439 | A | 3/1997 | Yoon |
| 5,611,576 | A | 3/1997 | Guala |
| 5,616,203 | A | 4/1997 | Stevens |
| 5,636,660 | A | 6/1997 | Pfleiderer et al. |
| 5,641,010 | A | 6/1997 | Maier |
| 5,645,538 | A | 7/1997 | Richmond |
| 5,647,845 | A | 7/1997 | Haber et al. |
| 5,651,776 | A | 7/1997 | Appling et al. |
| 5,653,686 | A | 8/1997 | Coulter et al. |
| 5,674,195 | A | 10/1997 | Truthan |
| 5,676,346 | A | 10/1997 | Leinsing |
| 5,685,845 | A | 11/1997 | Grimard |
| 5,699,821 | A | 12/1997 | Paradis |
| 5,702,019 | A | 12/1997 | Grimard |
| 5,718,346 | A | 2/1998 | Weiler |
| D393,722 | S | 4/1998 | Fangrow, Jr. et al. |
| 5,738,144 | A | 4/1998 | Rogers |
| 5,743,312 | A | 4/1998 | Pfeifer et al. |
| 5,746,733 | A | 5/1998 | Capaccio et al. |
| 5,755,696 | A | 5/1998 | Caizza |
| 5,766,211 | A | 6/1998 | Wood et al. |
| 5,772,630 | A | 6/1998 | Ljungquist |
| 5,772,652 | A | 6/1998 | Zielinski |
| RE35,841 | E | 7/1998 | Frank et al. |
| 5,776,116 | A | 7/1998 | Lopez et al. |
| 5,782,872 | A | 7/1998 | Muller |
| 5,806,831 | A | 9/1998 | Paradis |
| 5,817,082 | A | 10/1998 | Niedospial, Jr. et al. |
| 5,820,621 | A | 10/1998 | Yale et al. |
| 5,827,262 | A | 10/1998 | Neftel et al. |
| 5,832,971 | A | 11/1998 | Yale et al. |
| 5,833,213 | A | 11/1998 | Ryan |
| 5,834,744 | A | 11/1998 | Risman |
| 5,839,715 | A | 11/1998 | Leinsing |
| 5,853,406 | A | 12/1998 | Masuda et al. |
| 5,871,110 | A | 2/1999 | Grimard et al. |
| 5,873,872 | A | 2/1999 | Thibault et al. |
| 5,879,337 | A | 3/1999 | Kuracina et al. |
| 5,879,345 | A | 3/1999 | Aneas |
| 5,887,633 | A | 3/1999 | Yale et al. |
| 5,890,610 | A | 4/1999 | Jansen et al. |
| 5,891,129 | A | 4/1999 | Daubert et al. |
| 5,893,397 | A | 4/1999 | Peterson et al. |
| 5,897,526 | A | 4/1999 | Vaillancourt |
| 5,899,468 | A * | 5/1999 | Apps et al. ................. 280/47.26 |
| 5,902,280 | A | 5/1999 | Powles et al. |
| 5,902,298 | A | 5/1999 | Niedospial, Jr. et al. |
| 5,911,710 | A | 6/1999 | Barry et al. |
| 5,919,182 | A | 7/1999 | Avallone |
| 5,921,419 | A | 7/1999 | Niedospial, Jr. et al. |
| 5,924,584 | A | 7/1999 | Hellstrom et al. |
| 5,925,029 | A | 7/1999 | Jansen et al. |
| 5,935,112 | A | 8/1999 | Stevens et al. |
| 5,941,848 | A | 8/1999 | Nishimoto et al. |
| 5,944,700 | A | 8/1999 | Nguyen et al. |
| 5,954,104 | A | 9/1999 | Daubert et al. |
| 5,971,181 | A | 10/1999 | Niedospial, Jr. et al. |
| 5,971,965 | A | 10/1999 | Mayer |
| 5,989,237 | A | 11/1999 | Fowles et al. |
| 6,003,566 | A | 12/1999 | Thibault et al. |
| 6,004,278 | A | 12/1999 | Botich et al. |
| 6,019,750 | A | 2/2000 | Fowles et al. |
| 6,022,339 | A | 2/2000 | Fowles et al. |
| 6,036,171 | A | 3/2000 | Weinheimer et al. |
| 6,039,093 | A | 3/2000 | Mrotzek et al. |
| 6,039,302 | A | 3/2000 | Cote, Sr. et al. |
| D422,357 | S | 4/2000 | Niedospial, Jr. et al. |
| 6,063,068 | A | 5/2000 | Fowles et al. |
| D427,308 | S | 6/2000 | Zinger |
| 6,070,623 | A | 6/2000 | Aneas |
| 6,071,270 | A | 6/2000 | Fowles et al. |
| 6,080,132 | A | 6/2000 | Cole et al. |
| 6,089,541 | A | 7/2000 | Weinheimer et al. |
| 6,090,091 | A | 7/2000 | Fowles et al. |
| 6,090,093 | A | 7/2000 | Thibault et al. |
| 6,099,511 | A | 8/2000 | Devos et al. |
| 6,113,068 | A | 9/2000 | Ryan |
| 6,113,583 | A | 9/2000 | Fowles et al. |
| 6,117,114 | A | 9/2000 | Paradis |
| 6,139,534 | A | 10/2000 | Niedospial, Jr. et al. |
| 6,142,446 | A | 11/2000 | Leinsing |
| 6,146,362 | A | 11/2000 | Turnbull et al. |
| 6,156,025 | A | 12/2000 | Niedospial, Jr. et al. |
| 6,159,192 | A | 12/2000 | Fowles et al. |
| 6,168,037 | B1 | 1/2001 | Grimard |
| 6,171,287 | B1 | 1/2001 | Lynn et al. |
| 6,171,293 | B1 | 1/2001 | Rowley et al. |
| 6,173,852 | B1 | 1/2001 | Browne |
| 6,174,304 | B1 | 1/2001 | Weston |
| 6,179,822 | B1 | 1/2001 | Niedospial, Jr. |
| 6,179,823 | B1 | 1/2001 | Niedospial, Jr. |
| 6,206,861 | B1 | 3/2001 | Mayer |
| 6,221,041 | B1 | 4/2001 | Russo |
| 6,221,054 | B1 | 4/2001 | Martin et al. |
| 6,221,065 | B1 | 4/2001 | Davis |
| 6,238,372 | B1 | 5/2001 | Zinger et al. |
| 6,245,044 | B1 | 6/2001 | Daw et al. |
| D445,501 | S | 7/2001 | Niedospial, Jr. |
| D445,895 | S | 7/2001 | Svendsen |
| 6,253,804 | B1 | 7/2001 | Safabash |
| 6,258,078 | B1 | 7/2001 | Thilly |
| 6,280,430 | B1 | 8/2001 | Neftel et al. |
| 6,290,688 | B1 | 9/2001 | Lopez et al. |
| 6,296,621 | B1 | 10/2001 | Masuda et al. |
| 6,299,131 | B1 | 10/2001 | Ryan |
| 6,343,629 | B1 | 2/2002 | Wessman et al. |
| 6,348,044 | B1 | 2/2002 | Coletti et al. |
| 6,358,236 | B1 | 3/2002 | DeFoggi et al. |
| 6,364,866 | B1 | 4/2002 | Furr et al. |
| 6,378,576 | B2 | 4/2002 | Thibault et al. |
| 6,378,714 | B1 | 4/2002 | Jansen et al. |
| 6,379,340 | B1 | 4/2002 | Zinger et al. |
| 6,382,442 | B1 | 5/2002 | Thibault et al. |
| 6,408,897 | B1 | 6/2002 | Laurent et al. |
| 6,409,708 | B1 | 6/2002 | Wessman |
| 6,440,107 | B1 | 8/2002 | Trombley, III et al. |
| 6,453,949 | B1 | 9/2002 | Chau |
| 6,453,956 | B2 | 9/2002 | Safabash |
| 6,474,375 | B2 | 11/2002 | Spero et al. |
| 6,478,788 | B1 | 11/2002 | Aneas |
| D468,015 | S | 12/2002 | Horppu |
| 6,499,617 | B1 | 12/2002 | Niedospial, Jr. et al. |
| 6,503,240 | B1 | 1/2003 | Niedospial, Jr. et al. |
| 6,503,244 | B2 | 1/2003 | Hayman |
| 6,520,932 | B2 | 2/2003 | Taylor |
| 6,524,278 | B1 | 2/2003 | Campbell et al. |
| 6,524,295 | B2 | 2/2003 | Daubert et al. |
| D472,316 | S | 3/2003 | Douglas et al. |
| 6,530,903 | B2 | 3/2003 | Wang et al. |
| 6,537,263 | B1 | 3/2003 | Aneas |
| D472,630 | S | 4/2003 | Douglas et al. |
| 6,544,246 | B1 | 4/2003 | Niedospial, Jr. |
| 6,551,299 | B2 | 4/2003 | Miyoshi et al. |
| 6,558,365 | B2 | 5/2003 | Zinger et al. |
| 6,571,837 | B2 | 6/2003 | Jansen et al. |
| 6,572,591 | B2 | 6/2003 | Mayer |
| 6,575,955 | B2 | 6/2003 | Azzolini |
| 6,581,593 | B1 | 6/2003 | Rubin et al. |
| 6,582,415 | B1 | 6/2003 | Fowles et al. |
| 6,591,876 | B2 | 7/2003 | Safabash |
| 6,601,721 | B2 | 8/2003 | Jansen et al. |
| 6,626,309 | B1 | 9/2003 | Jansen et al. |
| D482,121 | S | 11/2003 | Harding et al. |

(56) References Cited

U.S. PATENT DOCUMENTS

D482,447 S 11/2003 Harding et al.
6,651,956 B2 11/2003 Miller
6,652,509 B1 11/2003 Helgren et al.
D483,487 S 12/2003 Harding et al.
D483,869 S 12/2003 Tran et al.
6,656,433 B2 12/2003 Sasso
6,666,852 B2 12/2003 Niedospial, Jr.
6,681,810 B2 1/2004 Weston
6,681,946 B1 1/2004 Jansen et al.
6,682,509 B2 1/2004 Lopez
6,692,478 B1 2/2004 Paradis
6,692,829 B2 2/2004 Stubler et al.
6,695,829 B2 2/2004 Hellstrom et al.
6,699,229 B2 3/2004 Zinger et al.
6,706,022 B1 3/2004 Leinsing et al.
6,706,031 B2 3/2004 Manera
6,715,520 B2 4/2004 Andreasson et al.
6,729,370 B2 5/2004 Norton et al.
6,736,798 B2 5/2004 Ohkubo et al.
6,745,998 B2 6/2004 Doyle
6,746,438 B1 6/2004 Arnissolle
6,752,180 B2 6/2004 Delay
D495,416 S 8/2004 Dimeo et al.
D496,457 S 9/2004 Prais et al.
6,802,490 B2 10/2004 Leinsing et al.
6,832,994 B2 12/2004 Niedospial, Jr. et al.
6,852,103 B2 2/2005 Fuller et al.
6,875,203 B1 4/2005 Fowles et al.
6,875,205 B2 4/2005 Leinsing
6,878,131 B2 4/2005 Novacek et al.
6,890,328 B2 5/2005 Fowles et al.
6,901,975 B2 6/2005 Aramata et al.
6,945,417 B2 9/2005 Jansen et al.
6,948,522 B2 9/2005 Newbrough et al.
6,949,086 B2 9/2005 Ferguson et al.
6,957,745 B2 10/2005 Thibault et al.
RE38,996 E 2/2006 Crawford et al.
6,994,315 B2 2/2006 Ryan et al.
6,997,916 B2 2/2006 Simas, Jr. et al.
6,997,917 B2 2/2006 Niedospial, Jr. et al.
7,024,968 B2 4/2006 Raudabough et al.
7,070,589 B2 7/2006 Lolachi et al.
7,074,216 B2 7/2006 Fowles et al.
7,083,600 B2 8/2006 Meloul
7,086,431 B2 8/2006 D'Antonio et al.
7,100,890 B2 9/2006 Cote, Sr. et al.
7,150,735 B2 12/2006 Hickle
7,192,423 B2 3/2007 Wong
7,195,623 B2 3/2007 Burroughs et al.
7,241,285 B1 7/2007 Dikeman
7,294,122 B2 11/2007 Kubo et al.
7,306,199 B2 12/2007 Leinsing et al.
D561,348 S 2/2008 Zinger et al.
7,326,188 B1 2/2008 Russell et al.
7,326,194 B2 2/2008 Zinger et al.
7,350,764 B2 4/2008 Raybuck
7,354,422 B2 4/2008 Riesenberger et al.
7,354,427 B2 4/2008 Fangrow
7,425,209 B2 9/2008 Fowles et al.
7,435,246 B2 10/2008 Zihlmann
7,452,348 B2 11/2008 Hasegawa
7,470,257 B2 12/2008 Norton et al.
7,470,265 B2 12/2008 Brugger et al.
7,472,932 B2 1/2009 Weber et al.
7,488,297 B2 2/2009 Flaherty
7,491,197 B2 2/2009 Jansen et al.
7,497,848 B2 3/2009 Leinsing et al.
7,523,967 B2 4/2009 Steppe
7,530,546 B2 5/2009 Ryan et al.
D595,420 S 6/2009 Suzuki et al.
D595,421 S 6/2009 Suzuki et al.
7,540,863 B2 6/2009 Haindl
7,540,865 B2 6/2009 Griffin et al.
7,544,191 B2 6/2009 Peluso et al.
D595,862 S 7/2009 Suzuki et al.
D595,863 S 7/2009 Suzuki et al.
7,611,487 B2 11/2009 Woehr et al.
7,611,502 B2 11/2009 Daly
7,615,041 B2 11/2009 Sullivan et al.
7,628,779 B2 12/2009 Aneas
7,632,261 B2 12/2009 Zinger et al.
D608,900 S 1/2010 Giraud et al.
7,654,995 B2 2/2010 Warren et al.
7,695,445 B2 4/2010 Yuki
D616,090 S 5/2010 Kawamura
7,713,247 B2 5/2010 Lopez
7,717,886 B2 5/2010 Lopez
7,722,090 B2 5/2010 Burton et al.
D616,984 S 6/2010 Gilboa
7,731,678 B2 6/2010 Tennican et al.
7,743,799 B2 6/2010 Mosler et al.
7,758,082 B2 7/2010 Weigel et al.
7,762,524 B2 7/2010 Cawthon et al.
7,766,304 B2 8/2010 Phillips
7,771,383 B2 8/2010 Truitt et al.
7,799,009 B2 9/2010 Niedospial, Jr. et al.
7,803,140 B2 9/2010 Fangrow, Jr.
D627,216 S 11/2010 Fulginiti
D630,732 S 1/2011 Lev et al.
7,862,537 B2 1/2011 Zinger et al.
7,867,215 B2 1/2011 Akerlund et al.
7,879,018 B2 2/2011 Zinger et al.
D634,007 S 3/2011 Zinger et al.
7,900,659 B2 3/2011 Whitley et al.
D637,713 S 5/2011 Nord et al.
D644,104 S 8/2011 Maeda et al.
7,993,328 B2 8/2011 Whitley
8,016,809 B2 9/2011 Zinger et al.
8,025,653 B2 9/2011 Capitaine et al.
8,029,472 B2 10/2011 Leinsing et al.
8,038,123 B2 10/2011 Ruschke et al.
8,066,688 B2 11/2011 Zinger et al.
8,070,739 B2 12/2011 Zinger et al.
8,096,525 B2 1/2012 Ryan
8,105,314 B2 1/2012 Fangrow, Jr.
D655,017 S 2/2012 Mosler et al.
8,122,923 B2 2/2012 Kraus et al.
D655,071 S 3/2012 Davila
8,157,784 B2 4/2012 Rogers
8,167,863 B2 5/2012 Yow
8,172,824 B2 5/2012 Pfeifer et al.
8,177,768 B2 5/2012 Leinsing
8,182,452 B2 5/2012 Mansour et al.
8,197,459 B2 6/2012 Jansen et al.
8,211,069 B2 7/2012 Fangrow, Jr.
8,225,959 B2 7/2012 Lambrecht
8,241,268 B2 8/2012 Whitley
8,262,628 B2 9/2012 Fangrow, Jr.
D669,980 S 10/2012 Lev et al.
8,287,513 B2 10/2012 Ellstrom et al.
D674,088 S 1/2013 Lev et al.
8,480,646 B2 7/2013 Nord et al.
8,506,548 B2 8/2013 Okiyama
8,523,837 B2 9/2013 Wiggins et al.
8,545,476 B2 10/2013 Ariagno et al.
8,551,067 B2 10/2013 Zinger et al.
8,556,879 B2 10/2013 Okiyama
2001/0000347 A1 4/2001 Hellstrom et al.
2001/0025671 A1 10/2001 Safabash
2001/0029360 A1 10/2001 Miyoshi et al.
2001/0051793 A1 12/2001 Weston
2002/0017328 A1 2/2002 Loo
2002/0066715 A1 6/2002 Niedospial
2002/0087118 A1 7/2002 Reynolds et al.
2002/0087141 A1 7/2002 Zinger et al.
2002/0087144 A1 7/2002 Zinger et al.
2002/0121496 A1 9/2002 Thiebault et al.
2002/0123736 A1 9/2002 Fowles et al.
2002/0127150 A1 9/2002 Sasso
2002/0128628 A1 9/2002 Fathallah
2002/0173752 A1 11/2002 Polzin
2002/0193777 A1 * 12/2002 Aneas ........................... 604/411
2003/0028156 A1 2/2003 Juliar
2003/0036725 A1 2/2003 Lavi et al.

(56) References Cited

U.S. PATENT DOCUMENTS

| | | | | |
|---|---|---|---|---|
| 2003/0068354 | A1 | 4/2003 | Reif et al. | |
| 2003/0073971 | A1 | 4/2003 | Saker | |
| 2003/0100866 | A1 | 5/2003 | Reynolds | |
| 2003/0120209 | A1 | 6/2003 | Jensen et al. | |
| 2003/0153895 | A1 | 8/2003 | Leinsing | |
| 2003/0187420 | A1 | 10/2003 | Akerlund et al. | |
| 2003/0191445 | A1 | 10/2003 | Wallen et al. | |
| 2003/0195479 | A1 | 10/2003 | Kuracina et al. | |
| 2003/0199846 | A1 | 10/2003 | Fowles et al. | |
| 2003/0199847 | A1 | 10/2003 | Akerlund et al. | |
| 2004/0024354 | A1 | 2/2004 | Reynolds | |
| 2004/0044327 | A1 | 3/2004 | Hasegawa | |
| 2004/0073189 | A1 | 4/2004 | Wyatt et al. | |
| 2004/0153047 | A1 | 8/2004 | Blank et al. | |
| 2004/0181192 | A1 | 9/2004 | Cuppy | |
| 2004/0204699 | A1 | 10/2004 | Hanly et al. | |
| 2004/0217315 | A1 | 11/2004 | Doyle | |
| 2004/0236305 | A1 | 11/2004 | Jansen et al. | |
| 2005/0015070 | A1 | 1/2005 | Delnevo et al. | |
| 2005/0055008 | A1 | 3/2005 | Paradis et al. | |
| 2005/0124964 | A1 | 6/2005 | Niedospial et al. | |
| 2005/0137566 | A1 | 6/2005 | Fowles et al. | |
| 2005/0148994 | A1 | 7/2005 | Leinsing | |
| 2005/0159724 | A1 | 7/2005 | Enerson | |
| 2005/0182383 | A1 | 8/2005 | Wallen | |
| 2005/0261637 | A1 | 11/2005 | Miller | |
| 2006/0030832 | A1* | 2/2006 | Niedospial et al. | 604/411 |
| 2006/0079834 | A1 | 4/2006 | Tennican et al. | |
| 2006/0089594 | A1 | 4/2006 | Landau | |
| 2006/0089603 | A1 | 4/2006 | Truitt et al. | |
| 2006/0095015 | A1 | 5/2006 | Hobbs et al. | |
| 2006/0106360 | A1 | 5/2006 | Wong | |
| 2006/0135948 | A1 | 6/2006 | Varma | |
| 2006/0253084 | A1 | 11/2006 | Nordgren | |
| 2007/0024995 | A1 | 2/2007 | Hayashi | |
| 2007/0060904 | A1* | 3/2007 | Vedrine et al. | 604/411 |
| 2007/0079894 | A1 | 4/2007 | Kraus et al. | |
| 2007/0083164 | A1 | 4/2007 | Barrelle et al. | |
| 2007/0088252 | A1 | 4/2007 | Pestotnik et al. | |
| 2007/0088293 | A1 | 4/2007 | Fangrow | |
| 2007/0088313 | A1 | 4/2007 | Zinger et al. | |
| 2007/0106244 | A1 | 5/2007 | Mosler et al. | |
| 2007/0112324 | A1 | 5/2007 | Hamedi-Sangsari | |
| 2007/0156112 | A1* | 7/2007 | Walsh | 604/415 |
| 2007/0167904 | A1 | 7/2007 | Zinger et al. | |
| 2007/0191760 | A1 | 8/2007 | Iguchi et al. | |
| 2007/0191764 | A1 | 8/2007 | Zihlmann | |
| 2007/0191767 | A1 | 8/2007 | Hennessy et al. | |
| 2007/0219483 | A1 | 9/2007 | Kitani et al. | |
| 2007/0244461 | A1 | 10/2007 | Fangrow | |
| 2007/0244462 | A1 | 10/2007 | Fangrow | |
| 2007/0244463 | A1 | 10/2007 | Warren et al. | |
| 2007/0249995 | A1 | 10/2007 | Van Manen | |
| 2007/0255202 | A1 | 11/2007 | Kitani et al. | |
| 2007/0265574 | A1 | 11/2007 | Tennican et al. | |
| 2007/0265581 | A1 | 11/2007 | Funamura et al. | |
| 2007/0270778 | A9 | 11/2007 | Zinger et al. | |
| 2007/0287953 | A1 | 12/2007 | Ziv et al. | |
| 2007/0299404 | A1 | 12/2007 | Katoh et al. | |
| 2008/0009789 | A1 | 1/2008 | Zinger et al. | |
| 2008/0009822 | A1 | 1/2008 | Enerson | |
| 2008/0172024 | A1 | 7/2008 | Yow | |
| 2008/0249479 | A1 | 10/2008 | Zinger et al. | |
| 2008/0249498 | A1 | 10/2008 | Fangrow | |
| 2008/0287905 | A1 | 11/2008 | Hiejima et al. | |
| 2008/0294100 | A1 | 11/2008 | de Costa et al. | |
| 2008/0306439 | A1 | 12/2008 | Nelson et al. | |
| 2008/0312634 | A1 | 12/2008 | Helmerson et al. | |
| 2009/0012492 | A1 | 1/2009 | Zihlmann | |
| 2009/0082750 | A1 | 3/2009 | Denenburg et al. | |
| 2009/0143758 | A1 | 6/2009 | Okiyama | |
| 2009/0177177 | A1 | 7/2009 | Zinger et al. | |
| 2009/0177178 | A1 | 7/2009 | Pedersen | |
| 2009/0187140 | A1 | 7/2009 | Racz | |
| 2009/0216212 | A1 | 8/2009 | Fangrow, Jr. | |
| 2009/0267011 | A1 | 10/2009 | Hatton et al. | |
| 2009/0299325 | A1 | 12/2009 | Vedrine et al. | |
| 2009/0326506 | A1 | 12/2009 | Hasegawa et al. | |
| 2010/0010443 | A1 | 1/2010 | Morgan et al. | |
| 2010/0022985 | A1 | 1/2010 | Sullivan et al. | |
| 2010/0030181 | A1 | 2/2010 | Helle et al. | |
| 2010/0036319 | A1 | 2/2010 | Drake et al. | |
| 2010/0076397 | A1 | 3/2010 | Reed et al. | |
| 2010/0087786 | A1 | 4/2010 | Zinger et al. | |
| 2010/0137827 | A1 | 6/2010 | Warren et al. | |
| 2010/0168712 | A1 | 7/2010 | Tuckwell et al. | |
| 2010/0179506 | A1 | 7/2010 | Shemesh et al. | |
| 2010/0204670 | A1 | 8/2010 | Kraushaar et al. | |
| 2010/0241088 | A1 | 9/2010 | Ranalletta et al. | |
| 2010/0274184 | A1 | 10/2010 | Chun | |
| 2010/0286661 | A1 | 11/2010 | Raday et al. | |
| 2010/0312220 | A1 | 12/2010 | Kalitzki | |
| 2011/0054440 | A1 | 3/2011 | Lewis | |
| 2011/0224640 | A1 | 9/2011 | Kuhn et al. | |
| 2011/0230856 | A1 | 9/2011 | Kyle et al. | |
| 2011/0264069 | A1 | 10/2011 | Bochenko | |
| 2011/0276007 | A1 | 11/2011 | Denenburg | |
| 2011/0319827 | A1 | 12/2011 | Leinsing et al. | |
| 2012/0022469 | A1 | 1/2012 | Alpert | |
| 2012/0053555 | A1 | 3/2012 | Ariagno et al. | |
| 2012/0059346 | A1 | 3/2012 | Sheppard et al. | |
| 2012/0078214 | A1 | 3/2012 | Finke et al. | |
| 2012/0123382 | A1 | 5/2012 | Kubo | |
| 2012/0184938 | A1 | 7/2012 | Lev et al. | |
| 2012/0215182 | A1 | 8/2012 | Mansour et al. | |
| 2012/0220977 | A1 | 8/2012 | Yow | |
| 2012/0220978 | A1 | 8/2012 | Lev et al. | |
| 2012/0265163 | A1 | 10/2012 | Cheng et al. | |
| 2012/0310203 | A1 | 12/2012 | Khaled et al. | |
| 2013/0053814 | A1 | 2/2013 | Mueller-Beckhaus et al. | |
| 2013/0096493 | A1 | 4/2013 | Kubo et al. | |
| 2013/0199669 | A1 | 8/2013 | Moy et al. | |

FOREIGN PATENT DOCUMENTS

| | | | |
|---|---|---|---|
| DE | 19504413 | A1 | 8/1996 |
| DE | 202004012714 | U1 | 11/2004 |
| DE | 202009011019 | U1 | 12/2010 |
| EP | 0192661 | A1 | 9/1986 |
| EP | 0195018 | A1 | 9/1986 |
| EP | 0258913 | A2 | 3/1988 |
| EP | 0416454 | A2 | 3/1991 |
| EP | 0518397 | A1 | 12/1992 |
| EP | 0521460 | A1 | 1/1993 |
| EP | 0637443 | A1 | 2/1995 |
| EP | 0737467 | A1 | 10/1996 |
| EP | 761562 | A1 | 3/1997 |
| EP | 765652 | A1 | 4/1997 |
| EP | 765853 | A1 | 4/1997 |
| EP | 0806597 | A1 | 11/1997 |
| EP | 0814866 | A1 | 1/1998 |
| EP | 829248 | A2 | 3/1998 |
| EP | 0856331 | A2 | 8/1998 |
| EP | 882441 | A2 | 12/1998 |
| EP | 897708 | A2 | 2/1999 |
| EP | 0898951 | A2 | 3/1999 |
| EP | 960616 | A2 | 12/1999 |
| EP | 1008337 | A1 | 6/2000 |
| EP | 1029526 | A1 | 8/2000 |
| EP | 1034809 | A1 | 9/2000 |
| EP | 1051988 | A2 | 11/2000 |
| EP | 1323403 | A1 | 7/2003 |
| EP | 1329210 | A1 | 7/2003 |
| EP | 1396250 | A1 | 3/2004 |
| EP | 1454609 | A1 | 9/2004 |
| EP | 1454650 | A1 | 9/2004 |
| EP | 1498097 | A2 | 1/2005 |
| EP | 1872824 | A1 | 1/2008 |
| EP | 1919432 | A1 | 5/2008 |
| EP | 1930038 | A2 | 6/2008 |
| EP | 2351548 | A1 | 8/2011 |
| EP | 2351549 | A1 | 8/2011 |
| FR | 2029242 | A5 | 10/1970 |
| FR | 2856660 | A1 | 12/2004 |

(56) References Cited

FOREIGN PATENT DOCUMENTS

| | | | |
|---|---|---|---|
| FR | 2869795 | A1 | 11/2005 |
| FR | 2931363 | A1 | 11/2009 |
| GB | 1444210 | A | 7/1976 |
| IL | 171662 | | 10/2005 |
| JP | 03-062426 | B | 9/1991 |
| JP | 4329954 | A | 11/1992 |
| JP | 06-050656 | U | 7/1994 |
| JP | H08-000710 | A | 1/1996 |
| JP | 09-104460 | A | 4/1997 |
| JP | 09-104461 | A | 4/1997 |
| JP | 10-118158 | A | 5/1998 |
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2001-505083 | A | 4/2001 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| JP | 2003-102807 | A | 4/2003 |
| JP | 2004-097253 | A | 4/2004 |
| JP | 2004-522541 | A | 7/2004 |
| WO | 9403373 | A1 | 2/1994 |
| WO | 9507066 | A1 | 3/1995 |
| WO | 9600053 | A1 | 1/1996 |
| WO | 96/29113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0236191 | A2 | 5/2002 |
| WO | 02089900 | A1 | 11/2002 |
| WO | 03051423 | A2 | 6/2003 |
| WO | 03079956 | A1 | 10/2003 |
| WO | 2004041148 | A1 | 5/2004 |
| WO | 2005002492 | A1 | 1/2005 |
| WO | 2005041846 | A2 | 5/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007105221 | A1 | 9/2007 |
| WO | 2009026443 | A2 | 2/2009 |
| WO | 2009029010 | A1 | 3/2009 |
| WO | 2009038860 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012143921 | A1 | 10/2012 |

OTHER PUBLICATIONS

Int'l Search Report issued Mar. 18, 2013 in Int'l Application No. PCT/IL2012/050516.
Office Action issued Apr. 2, 2013 in U.S. Appl. No. 13/505,790.
Int'l Search Report and Written Opinion issued Mar. 6, 2012 in Int'l Application No. PCT/IL2011/000834.
U.S. Appl. No. 13/883,289 by Lev, filed May 3, 2013.
U.S. Appl. No. 29/438,134 by Lev, filed Nov. 27, 2012.
U.S. Appl. No. 29/438,141 by Gilboa, filed Nov. 27, 2012.
Int'l Search Report & Written Opinion issued on Mar. 7, 2012 in Int'l Application No. PCT/IL2011/000829.
U.S. Appl. No. 13/884,981 by Denenburg, filed May 13, 2013.
Office Action issued May 31, 2013 in U.S. Appl. No. 13/505,790.
Office Action issued Mar. 1, 2012 in JP Application No. 2007-510229.
Int'l Search Report issued Mar. 7, 2012 in Int'l Application No. PCT/IL2011/000829; Written Opinion.
Office Action issued Mar. 13, 2012 in CA Application No. 2,563,643.
Office Action issued Mar. 1, 2012 in CN Application No. 200880110828З.4.
Office Action issued Mar. 6, 2012 in U.S. Appl. No. 12/678,928.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
Office Action issued Jun. 14, 2012 in U.S. Appl. No. 29/376,980.
Office Action issued Jun. 15, 2012 in U.S. Appl. No. 29/413,170.
Office Action issued Jun. 21, 2012 in U.S. Appl. No. 12/596,167.
Int'l Search Report issued Aug. 16, 2012 in Int'l Application No. PCT/IL2012/000164.
Int'l Search Report issued Jun. 19, 2013 in Int'l Application No. PCT/IL2013/050167.
Int'l Preliminary Report on Patentability issued Aug. 28, 2012 in Int'l Application No. PCT/IL2011/000186.
U.S. Appl. No. 14/005,751 by Denenburg, filed Sep. 17, 2013.
English translation of an Office Action issued Jul. 26, 2013 in JP Application No. 2012-538464.
International Search Report Issued Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Office Action Issued Jun. 8, 2010 in U.S. Appl. No. 12/112,490 by Zinger.
Office Action issued Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Office Action issued Jun. 15, 2011 in JP Application No. 2008-538492.
Translation of Office Action issued Jun. 18, 2012 in JP Application No. 2008-538492.
Translation of Office Action issued Apr. 15, 2013 in JP Application No. 2008-538492.
Office Action issued Jul. 13, 2012 in U.S. Appl. No. 12/112,490 by Zinger.
Office Action issued Jan. 23, 2013 in U.S. Appl. No. 12/112,490 by Zinger.
Int'l Preliminary Report on Patentability issued May 6, 2008 in Int'l Application No. PCT/IL2006/001228.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ultrasite.rtm. Valve, B. Braun Medical, Inc. website and product description, 3 pages, Feb. 2006.
Office Action Issued Oct. 6, 2003 in U.S. Appl. No. 10/062,796.

(56) References Cited

OTHER PUBLICATIONS

Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/Pages/Mixject.aspx, dated Aug. 8, 2012.
Int'l Search Report Issued Jul. 27, 2007 in Int'l Application No. PCT/IL2007/000343.
http://www.westpharma.com/eu/en/products/Pages/Mixject.aspx.
http://www.westpharma.com/eu/SiteCollectionDocuments/Recon/mixject%20product%20sheet.pfg; Mixject product information sheet pp. 1.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCTT/IL2005/000376.
Written Opinion of ISR Issued in Int'l Application No. PCT/IL2005/000376, Issued Oct. 29, 2006.
Int'l Search Report Issued Aug. 25, 2008 in Int'l Application No. PCT/IL2008/000517.
Written Opinion of the ISR Issued Oct. 17, 2009 in Int'l Application No. PCT/IL08/00517.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued Jan. 20, 2010 in JP Application No. 2007-510229.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Office Action issued Jun. 1, 2010 in U.S. Appl. No. 11/568,421.
Office Action issued Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Nov. 29, 2010 in U.S. Appl. No. 11/568,421.
Office Action issued Dec. 23, 2010 in U.S. Appl. No. 29/334,696.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.
Office Action issued Jul. 11, 2011 in U.S. Appl. No. 12/293,122.
Int'l Search Report issued Jul. 12, 2011 in Int'l Application No. PCT/IL2011/000187.
Int'l Search Report issued Jul. 12, 2011 in Int'l Application No. PCT/IL2011/000186.
Office Action issued Aug. 3, 2011 in JP Application No. 2008-525719.
Int'l Search Report issued Oct. 7, 2011 in Int'l Application No. PCT/IL2011/000511.
Int'l Search Report issued Mar. 6, 2012 in Int'l Application No. PCT/IL2011/000834; Written Opinion.
Written Opinion issued Aug. 16, 2012 in Int'l Application No. PCT/IL2012/000164.
English translation of an Office Action issued Sep. 10, 2013 in JP Application No. 2012-554468.
Int'l Search Report issued Jun. 5, 2013 in Int'l Application No. PCT/IL2012/050407.
Int'l Search Report issued Jun. 19, 2013 in Int'l Application No. PCT/IL201/050167.
Int'l Search Report issued Jul. 1, 2013 in Int'l Application No. PCT/IL2013/050180.
Int'l Search Report issued Jul. 31, 2103 in Int'l Application No. PCT/IL2013/050313.
Int'l Search Report issued Jul. 26, 2013 in Int'l Application No. PCT/IL2013/050316.
English translation of an Office Action issued Jun. 19, 2013 in JP Application No. 2012-531551.
Office Action issued Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action issued Jan. 2, 2014 in U.S. Appl. No. 13/505,881 by Lev.

* cited by examiner

LIQUID DRUG TRANSFER DEVICE WITH VENTED VIAL ADAPTER

CROSS-REFERENCE TO RELATED APPLICATION

This application is a Section 371 of International Application No. PCT/IL2011/000187, filed Feb. 23, 2011, which was published in the English language on Sep. 1, 2011, under International Publication No. WO 2011/104712 A1, and the disclosure of which is incorporated herein by reference.

FIELD OF THE INVENTION

The invention relates to liquid drug transfer devices in general and liquid drug transfer devices including a vented vial adapter in particular.

BACKGROUND OF THE INVENTION

U.S. Pat. No. 6,139,534 to Niedospial, Jr. et al. illustrates and describes a liquid drug transfer device constituted by a vented vial adapter having a longitudinal vial adapter axis and including a top wall with a series of axial directed vent apertures, an annular air filter underlying the series of vent apertures, a downward depending skirt for telescopically receiving a vial therein, a downward depending central dual lumen puncturing spike and an oppositely directed central liquid transfer port. The dual lumen puncturing spike includes a pair of axial directed adjacent lumens, namely, a liquid transfer lumen and a vent lumen. The liquid transfer port is in flow communication with the liquid transfer lumen. The vent apertures are in flow communication with the vent lumen via the air filter. The vented vial adapter includes an elastomeric pre-split septum for maintaining sterility of vial contents. Use of the vented vial adapter may lead to liquid contents inadvertently draining into one or more of the vent apertures or one or more vent apertures being splashed by liquid contents, thereby wetting the underlying air filter to the detriment of its operation.

Liquid drug transfer devices with vented vial adapters are also illustrated and described in inter alia U.S. Pat. No. 4,834,744 to Ritson, U.S. Pat. Nos. 6,503,240, 6,544,246, 6,655,246, 6,997,917 and 7,799,009 also to Niedospial, Jr. et al., U.S. Pat. No. 7,192,423 to Wong, U.S. Pat. No. 7,452,348 to Hasegawa, US Patent Application Publication No. US 2007/0156112 to Walsh, US Patent Application Publication No. US 2008/0172024 to Yow.

SUMMARY OF THE INVENTION

The present invention is directed toward liquid drug transfer devices including a hitherto described vented vial adapter. The present invention is directed towards provisioning such a vented vial adapter with individual protective hoods for covering its vent apertures for precluding liquid drug contents entering a vent aperture due to draining, splashing, and the like, and wetting its underlying air filter to the detriment of its operation. The present invention can include a manually placed cap for placing on a liquid access port for maintaining contents sterility. Alternatively, the present invention can include an elastomeric pre-split septum for maintaining sterility of vial contents.

The present invention can be equally applied to a wide range of liquid drug transfer devices including vented vial adapters for use with different sized vials, namely, 13 mm, 20 mm, and the like. The liquid drug transfer devices can be constituted by vial adapters per se including female vial adapters, male vial adapters, and the like. Other liquid drug transfer devices include, for example, liquid drug transfer devices illustrated and described in commonly owned U.S. Pat. No. 6,558,365 to Zinger et al., in-line liquid drug transfer devices illustrated and described in commonly owned PCT International Publication No. WO 2005/105014, and the like.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figure 1:
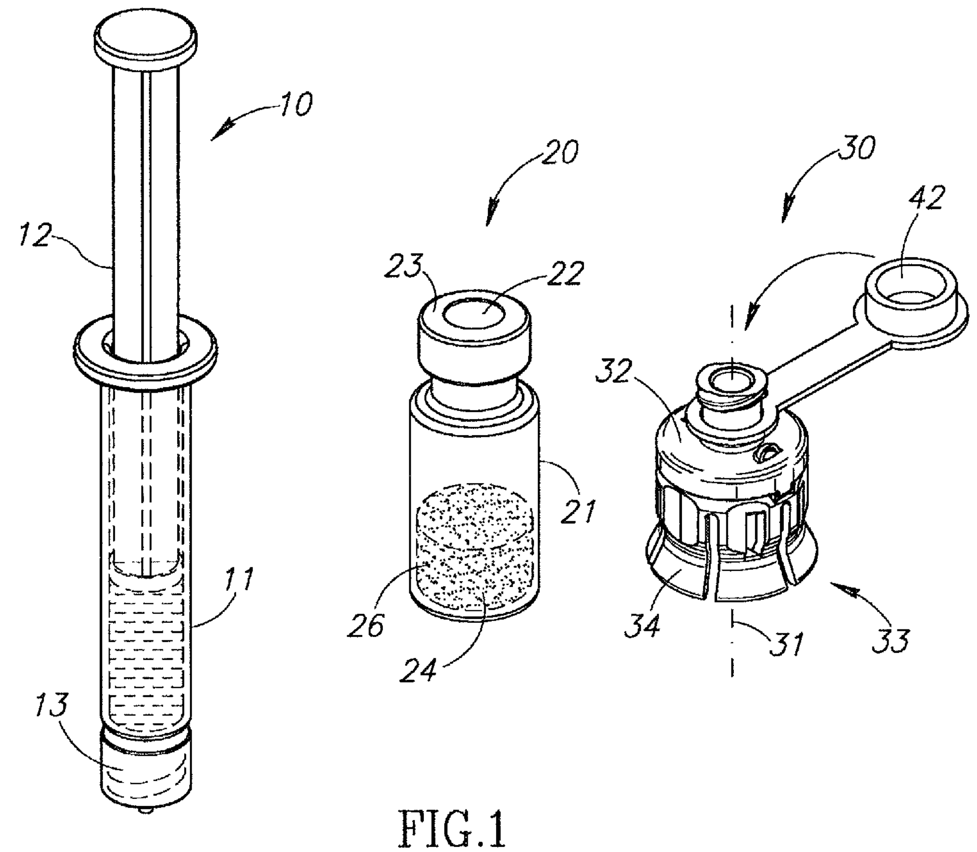
FIG. 1 is a pictorial representation of a syringe, a vial and a vented female vial adapter having a longitudinal vial axis.

FIG. 1 shows a syringe 10 constituting a source of physiological fluid, a medicinal vial 20 and a liquid drug transfer device 30 constituted by a vented female vial adapter for use with the syringe 10 and the vial 20. The syringe 10 includes a barrel 11 with a plunger 12 and a male Luer lock connector 13. The syringe 10 can be formed with other types of male connectors. The vial 20 includes an open topped bottle 21 sealed by a vial stopper 22 capped by a metal band 23. The vial 20 contains either a powdered or liquid drug 24 under negative pressure. The syringe 10 typically contains diluent for reconstituting the vial contents 24.

FIGS. 1 to 4 show the vented female vial adapter 30 has a longitudinal vial adapter axis 31 and includes a transverse top wall 32 having a downward depending skirt 33 with flex members 34 for snap fitting onto the vial 20. The vial adapter 30 includes a downward depending dual lumen puncturing spike 36 for puncturing the vial stopper 22 on snap fitting the skirt 33 on the vial 20. The puncturing spike 36 includes a base 36A towards the top wall 32 and terminates in a spike tip 36B. The puncturing spike 36 includes a pair of axial directed lumens, namely, a liquid transfer lumen 37 and a vent lumen 38. The liquid transfer lumen 37 includes a port 37A towards the spike tip 36B. The vent lumen 38 has a port 38A towards the spike tip 36B.

The vial adapter 30 also includes a central axial directed liquid transfer port 39 oppositely directed to the puncturing spike 36 and in flow communication with the liquid transfer lumen 37. The liquid transfer port 39 terminates in a female Luer connector 41 for screw thread engagement with the syringe's male Luer lock connector 13. The vial adapter 30 includes a manually placed cap 42 for sealing the female Luer connector 41.

The top wall 32 includes a pair of diametrical opposite axial directed vent apertures 43. An annular air filter 44 is disposed beneath the top wall 32. The vent apertures 43 are in flow communication with the vent lumen 38 via the air filter 44. The air filter 44 filters air entering drawn into the vial 20 on puncturing the vial stopper 22.

Figure 2:
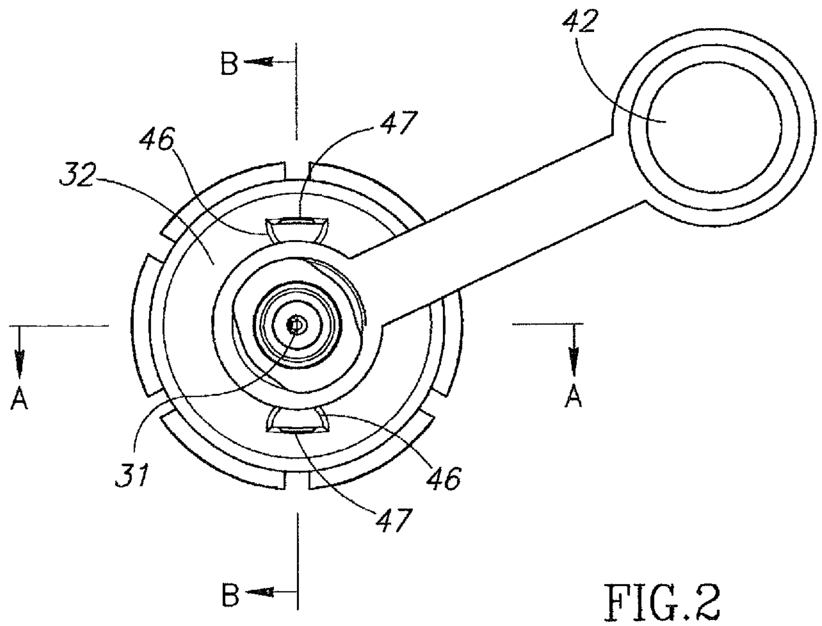
FIG. 2 is a top plan view of the vented vial adapter along the longitudinal vial axis.
Figure 3:
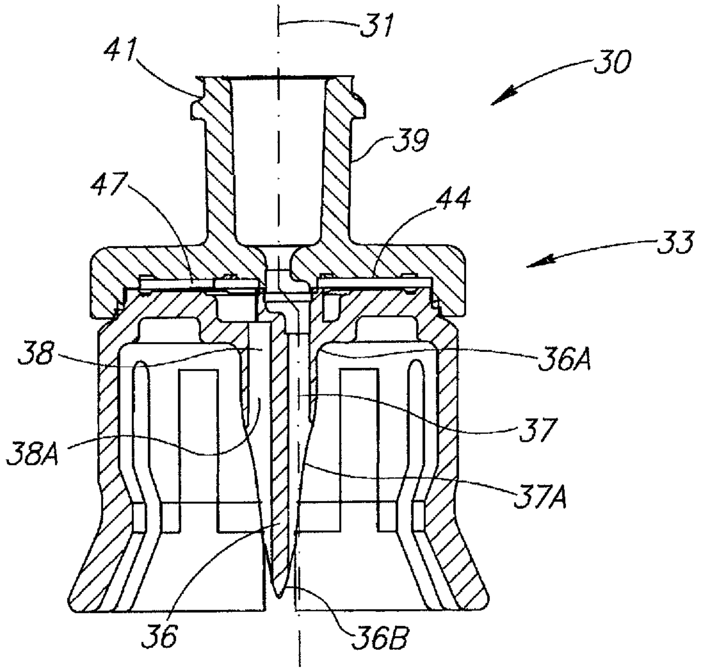
FIG. 3 is a longitudinal cross section of FIG. 1's vented vial adapter along line A-A in FIG. 2.
Figure 4:
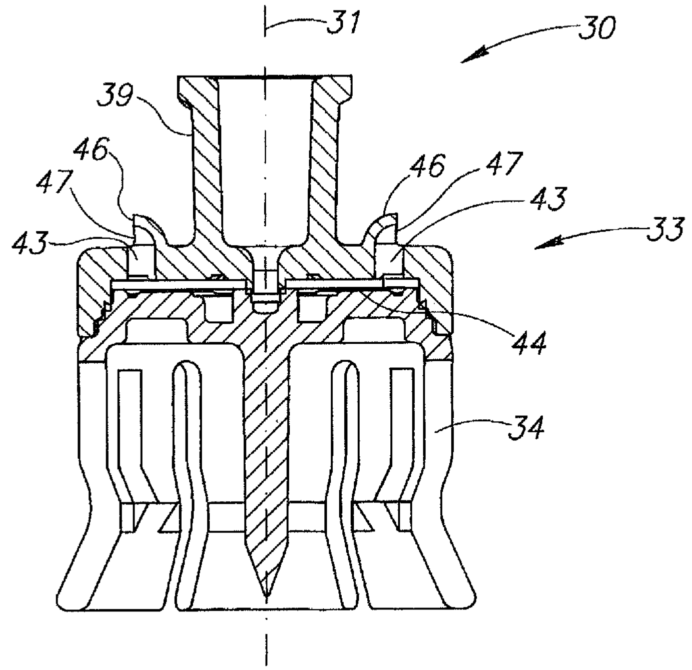
FIG. 4 is a longitudinal cross section of FIG. 1's vented vial adapter along line B-B in FIG. 2.

The top wall 32 is formed with a pair of protective hoods 46 mounted over the vent apertures 43 for covering the vent apertures 43 in FIG. 2's top plan view. The protective hoods 46 are preferably quarter sphere shaped. The protective hoods 46 each have a hood aperture 47 above the top wall 32 and facing radial outwards relative to the longitudinal vial adapter axis 31. The protective hoods 46 preclude liquid contents inadvertently wetting the air filter 44 via the vent apertures 43 during use of the vial adapter 30.

Figure 5:
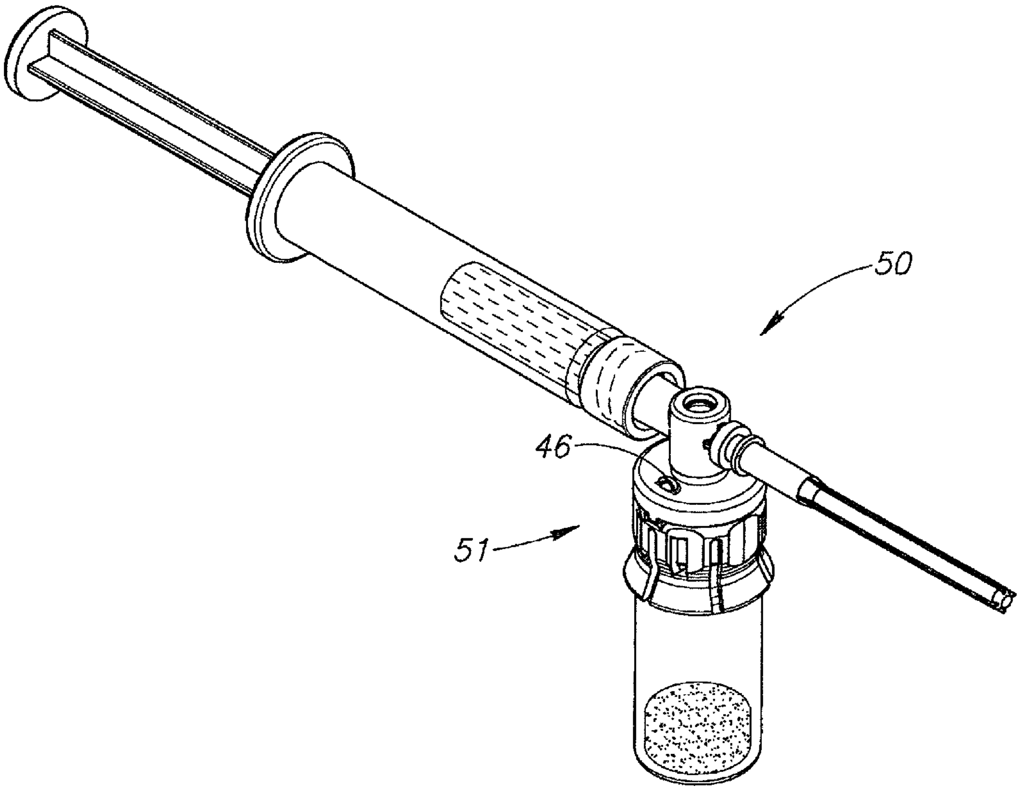
FIG. 5 is a pictorial representation of a liquid drug transfer device with a detachable vented vial adapter.

FIG. 5 shows a U.S. Pat. No. 6,558,365 liquid drug transfer device 50 with a detachable vented vial adapter 51 similar to the vented vial adapter 30.

While the invention has been described with respect to a limited number of embodiments, it will be appreciated that many variations, modifications, and other applications of the invention can be made within the scope of the appended claims.

The invention claimed is:

1. A liquid drug transfer device for use with a medicinal vial including a bottle containing a medicament, a vial opening stopped by a vial stopper, and a narrow neck intermediate the bottle and the vial opening, the liquid drug transfer device comprising:

a vented vial adapter having a longitudinal vial adapter axis and including a top wall transverse to said longitudinal adapter axis, a cylindrical skirt having flex members resiliently attached to said top wall and downwardly depending therefrom for telescopically slidingly receiving the vial opening therein, an annular air filter disposed beneath said top wall, said top wall having an upper surface and said cylindrical skirt having peripheral skirt surface, said upper surface meeting said peripheral skirt surface at an upper surface edge, a downwardly depending dual lumen puncturing spike for puncturing the vial stopper for establishing flow communication with the bottle interior said puncturing spike having a base adjacent said top wall and a puncturing tip, said puncturing tip including a pair of axial directed lumens extending from said base to said puncturing tip, said pair of axial directed lumens including a liquid transfer lumen and a vent lumen, a liquid transfer port in flow communication with said liquid transfer lumen, said liquid transfer port extending upwardly from said upper surface opposite said cylindrical skirt, at least two spaced apart axially directed vent apertures formed in said top wall and in flow communication with said vent lumen via said air filter, said liquid transfer port and said at least two spaced apart vent apertures being in flow communication with the bottle on slidingly receiving the vial in the vial adapter, wherein said top wall is formed with a corresponding number of at least two discrete protective hoods at said at least two vent apertures extending upwardly from said upper surface, opposite said cylindrical skirt, such that each of said at least two vent apertures is individually covered by a discrete protective hood in a top plan view of said vented vial adapter along said longitudinal vial adapter axis and each of said at least two discrete protective hoods (i) has a hood aperture facing radially outwardly with respect to said longitudinal vial adapter axis, and (ii) is visible in a side elevation view of said vented vial adapter intercepting said upper surface edge such that liquid contents inadvertently disposed on said upper surface of an inclined vented vial adapter are diverted around a discrete protective hood for draining over said upper surface edge and down said peripheral skirt surface, thereby inhibiting said inadvertently disposed liquid contents from inadvertently entering the corresponding vent aperture covered thereby and wetting said air filter.

2. The device according to claim 1, wherein each said protective hood has a quarter sphere shaped protective hood.

3. The device according to claim 1, further comprising a manually placed cap for sealing said liquid access port.

4. A liquid drug transfer device for use with a medicinal vial including a bottle containing a medicament, a vial opening stopped by a vial stopper, and a narrow neck intermediate the bottle and the vial opening, the liquid drug transfer device comprising a vented vial adapter having a longitudinal vial adapter axis and including a top wall transverse to said longitudinal axis, a cylindrical skirt having flex members resiliently attached to said top wall and downwardly depending therefrom for telescopically slidingly receiving the vial opening therein, an annular air filter disposed beneath said top wall, a downwardly depending dual lumen puncturing spike for puncturing the vial stopper and establishing flow communication with the bottle interior, said puncturing spike having a base adjacent said top wall and a puncturing tip, said puncturing tip including a pair of axially directed lumens extending from said base to said puncturing tip, said pair of axially directed lumens including a liquid transfer lumen and a vent lumen, a liquid transfer port in flow communication with said liquid transfer lumen, at least one axially directed vent aperture formed in said top wall and in flow communication with said vent lumen via said air filter, said liquid transfer port and said at least one vent aperture being in flow communication with the bottle on slidingly receiving the vial in the vial adapter wherein said top wall is formed with a corresponding number of at least one quarter-sphere shaped protective hood at said at least one vent aperture, such that each of said at least one vent aperture is individually covered by a protective hood in a top plan view of said vented vial adapter along said longitudinal vial adapter axis and each of said at least one protective hood has a hood aperture facing-radially outwardly with respect to said longitudinal vial adapter axis.

5. The device according to claim 4, further comprising a manually placed cap for sealing said liquid access port.

* * * * *